United States Patent [19]
Zoughi et al.

[11] Patent Number: 5,216,372
[45] Date of Patent: Jun. 1, 1993

[54] MICROWAVE STEEL BELT LOCATION SENSOR FOR TIRES

[75] Inventors: Reza Zoughi; Sasan Bakhtiari, both of Fort Collins, Colo.

[73] Assignee: Colorado State University Research Foundation, Fort Collins, Colo.

[21] Appl. No.: 960,238

[22] Filed: Oct. 13, 1992

Related U.S. Application Data

[63] Continuation of Ser. No. 737,344, Jul. 29, 1991, abandoned.

[51] Int. Cl.$^5$ ...................... G01M 17/02; E01C 23/00
[52] U.S. Cl. .................................. 324/644; 324/638; 324/642; 324/645; 73/146
[58] Field of Search .................. 73/146; 324/644, 645, 324/638, 639, 642

[56] References Cited

U.S. PATENT DOCUMENTS

| | | | |
|---|---|---|---|
| 2,442,606 | 6/1948 | Korman | 324/645 |
| 2,605,323 | 7/1952 | Samuel | 324/638 |
| 3,238,451 | 3/1966 | Shively | 324/638 |
| 3,549,986 | 12/1970 | Prine . | |
| 3,562,642 | 2/1971 | Hochschild | 324/642 |
| 3,622,874 | 11/1971 | Chasek | 324/642 |
| 3,648,164 | 3/1972 | Searle et al. . | |
| 3,796,948 | 3/1974 | Wentworth | 324/638 |
| 4,075,555 | 2/1978 | Wight | 324/644 |
| 4,224,624 | 9/1980 | Evans . | |
| 4,707,652 | 11/1987 | Lowitz . | |
| 4,818,930 | 4/1989 | Flemming | 324/643 |
| 4,936,529 | 6/1990 | Maine . | |

OTHER PUBLICATIONS

Caldecott, "The Generalized Multiprobe Reflectometer and Its Application to Automated Transmission Line Measurements", IEEE Transactions on Antennas and Propagation, vol. AP-21, No. 4, pp. 550-554, Jul. 1973.

Zoughi, et al., "Nondestructive Microwave Thickness Measurements of Dielectric Slabs", *Materials Evaluation*, vol. 48, No. 9, pp. 1100-1105, Sep. 1990.

*Primary Examiner*—Kenneth A. Wieder
*Assistant Examiner*—Jose M. Solis
*Attorney, Agent, or Firm*—Dorr, Carson, Sloan & Peterson

[57] ABSTRACT

The thickness of the layers of rubber covering the steel belts within a tire can be measured by transmitting a microwave signal toward the outer surface of the tire and measuring the phase shift of the signal reflected by the tire. In the preferred embodiment, a waveguide is used to direct the microwave signal toward the tire. A standing wave is created within the waveguide by interference between the transmitted microwave signal and the microwave signal reflected from the tire. A series of crystal detectors mounted along the length of the waveguide measure the standing wave. A processor calculates the phase of the reflection coefficient, and determines the thickness of the rubber layer as a predetermined function of the phase. By proper selection of the microwave frequency and the spacing between the waveguide and the tire, the rubber layer thickness can be uniquely determined as a function of phase for any range of rubber thicknesses likely to be encountered in a tire. In addition, a phase reversal (from 180° to −180°) can be arranged to occur at a specific rubber thickness by proper selection of these parameters. This can be used in the tire retreading process to halt buffing when a predetermined minimum rubber thickness has been reached.

14 Claims, 5 Drawing Sheets

MICROWAVE STEEL BELT LOCATION SENSOR FOR TIRES

RELATED APPLICATION

This application is a continuation of the Applicants' U.S. Pat. Application Ser. No. 07/737,344 filed on Jul. 29, 1991, now abandoned.

BACKGROUND OF THE INVENTION

1. Field of the Invention

The present invention relates generally to the field of thickness measurement. More specifically, the present invention discloses a sensor using microwave technology to precisely measure the thickness of the layers of rubber covering the steel belts within a tire as a function of the phase of the reflected microwave signal.

2. Statement of the Problem

Before a tire can be retread, it is necessary to remove any remaining tread. The conventional approach is to buff or cut the remaining tread rubber from the tire casing by means of rotating knives. Ideally, approximately 2 mm of rubber should be left covering the steel belts within the tire casing. One common problem is determination when enough rubber has been removed in the buffing operation. If too much rubber is removed and the steel belts are damaged, the tire casing must be discarded. The conventional solution is to periodically halt the buffing process and manually measure the depth of the remaining rubber by inserting a micrometer through the rubber until it contacts the steel belts within the tire. Manual measurement of rubber thickness is typically done only at one randomly selected point along the tire circumference. If the steel belts have a radial bulge in one region of the tire casing, a manual measurement will usually fail to halt the buffing process before the bulge in the steel belts is uncovered and damaged by the knives. In addition, manual measurement adds substantial delay and labor expense to the buffing process.

A number of devices and processes have been invented in the past using microwave technology to detect flaws in an object, such as a tire, including the following:

| Inventor | Patent No. | Issue Date |
| --- | --- | --- |
| Prine | 3,549,986 | Dec. 22, 1970 |
| Evans | 4,224,624 | Sep. 23, 1980 |
| Searle, et al. | 3,648,164 | March 7, 1972 |
| Maine | 4,936,529 | June 26, 1990 |
| Lowitz | 4,707,652 | Nov. 17, 1987 |

Prine discloses a system using microwaves for detection of flaws in a sample, such as a tire. The system has a transmitting antenna and a receiving antenna positioned with their polarization directions transverse to each other. The receiver is relatively insensitive to energy transmitted directly from the transmitting antenna and energy reflected from the surfaces of the sample, but is highly sensitive to energy scattered by flaws within the sample.

Evans discloses a system for detecting when a movable object is located in a predetermined position. Positioning is determined by detecting the change in polarization of microwave radiation reflected from the movable object.

Searle, et al., disclose a system for detecting variations in the spacing of an array of conducting strands (e.g. steel belts) within a rubber or plastics medium (e.g. a tire). A microwave transmitter is placed within the tire and a receiver is place outside (or vice versa). As the tire is rotated, any variation in the spacing of the steel belts will affect the intensity of the microwave signal transmitted through the tire to the receiver.

Maine discloses a device for detecting surface profile defects on metal wheels on rail cars. A resonator cavity mounted proximate to the rail causes reflection of microwave energy from the wheel surface. A microwave detector receives the reflected signal and determines surface profile detects by monitoring any changes in the reflected signal.

Lowitz discloses an impurity detector measuring parallel polarized scattered electromagnetic radiation through a bulk material. The detector responds to any change in signal intensity through the bulk material, thereby indicating the presence of an impurity which changes the effective bulk dielectric constant of the sample.

3. Solution to the Problem

None of the prior art references uncovered in the search disclose a means for precise measurement of the thickness of tire rubber as a function of the phase of the reflected microwave signal. The present invention allows precise nondestructive measurements of the thickness of the rubber layer without interrupting the buffing process. In addition, the present invention continuously measures the thickness of the rubber layer as the tire is rotated before the sensor, thereby identifying any bulges or other distortions in the steel belts within the tire casing.

SUMMARY OF THE INVENTION

This invention provides a method and apparatus for measuring the thickness of the layers of rubber covering the steel belts within a tire. A microwave signal is transmitted toward the outer surface of the tire, and the phase difference between the transmitted signal and the signal reflected by the tire is measured. In the preferred embodiment, a waveguide is used to direct the microwave signal toward the tire. A standing wave is created within the waveguide by interference between the transmitted signal and the signal reflected from the tire. A series of crystal detectors are mounted along the length of the waveguide to measure the standing wave. A processor calculates the phase of the reflection coefficient, and determines the thickness of the rubber layer as a predetermined function of the phase. By proper selection of the microwave frequency and the spacing between the waveguide and the tire, the thickness of the rubber layer can be uniquely determined as a function of phase for any range of rubber thicknesses likely to be encountered in a tire. In addition, a phase reversal (from 180° to −180°) can be arranged to occur at a specific rubber thickness by proper selection of these parameters. This can be used in the tire retreading process to halt buffing when a predetermined minimum rubber thickness has been reached.

A primary object of the present invention is to provide a method and apparatus to continually measure the thickness of the rubber layers covering the steel belts at all points along the circumference of the tire casing during the buffing process.

Another object of the present invention is to provide a method and apparatus for nondestructive and noninvasive measurement of the thickness of a layer of lossy, dielectric material backed by a layer of conductive material.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

In a situation where an electromagnetic wave impinges upon a plane of conductive material, the wave is reflected. Assuming the direction of propagation of the wave is normal to the conductive plane and the plane is a perfect conductor, the wave will be completely reflected normal to the conductive plane. Also, the reflected wave will have the same amplitude and phase as the incident wave. In such a situation, the magnitude of the reflection coefficient ($\Gamma = E_r/E_i$) is one, and phase of the reflection coefficient is $-180°$. Expressed as a complex number, $\Gamma = E_t/E_i$ in this case. The transmission coefficient ($\tau = E_t/E_i$) is zero. Interference between the incident wave and reflected wave traveling in opposite directions results in a standing wave in which both the electric and magnetic fields have regularly occurring zeroes (and maxima) at intervals of $\lambda/2$.

A more complicated situation arises where a layer of lossy, dielectric material (such as rubber) is placed in front of the conductive plane. In this case, a portion of the incident wave is reflected by the dielectric layer, a portion is transmitted through the dielectric layer to the conductive plane where it is reflected, and a portion is effectively absorbed by the dielectric layer. The net result is that the reflected wave is substantially attenuated in amplitude, and is shifted in phase with respect to the incident beam. In this case, the reflection coefficient is a complex number in which the imaginary component corresponds to the phase shift introduced by the dielectric layer. Since the reflected signal has a smaller amplitude than the incident signal, interference between the two signals does not produce a standing wave with zeroes, but rather produces a complex waveform having regularly occurring maxima and minima.

Figure 1:
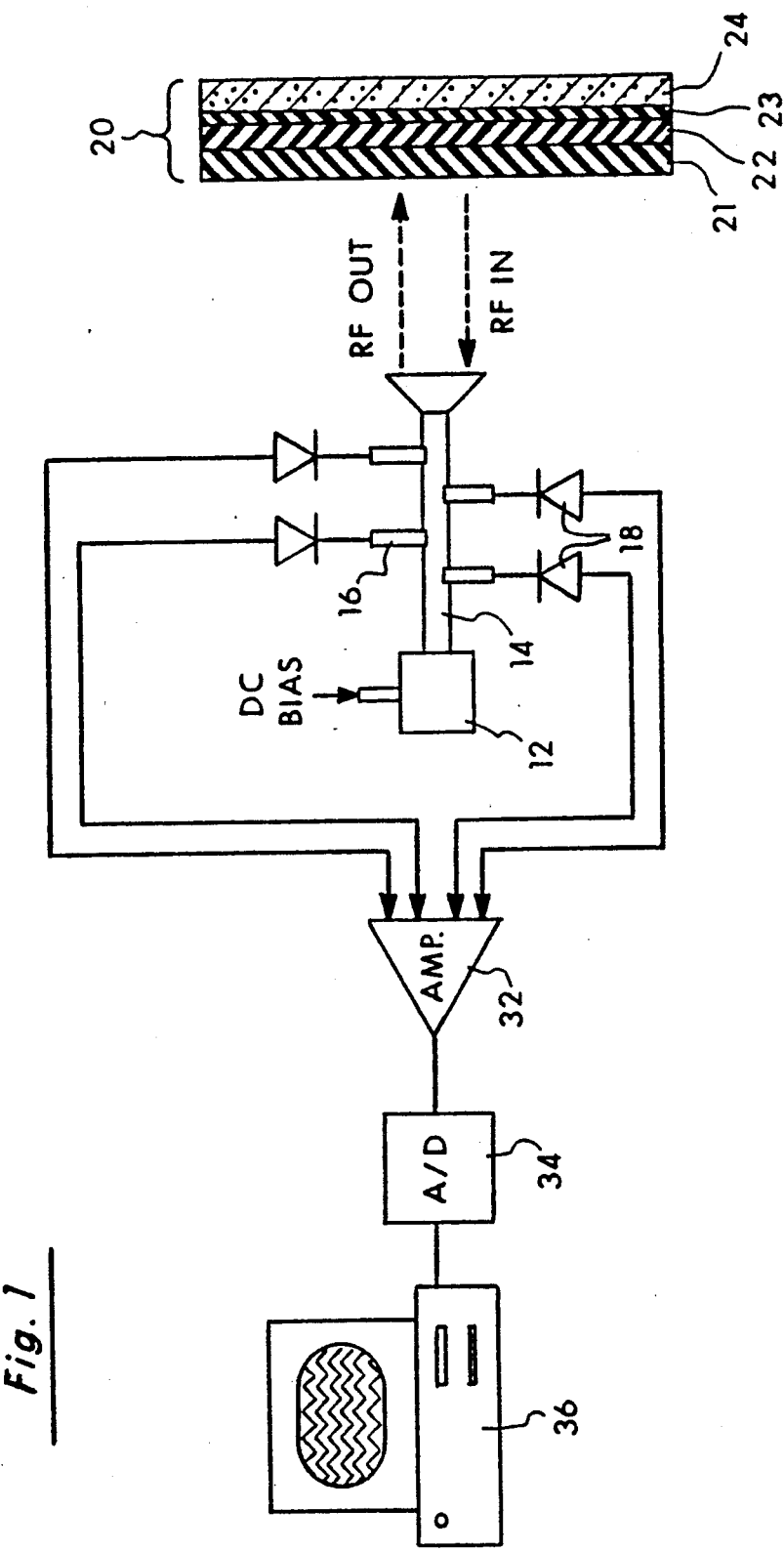
FIG. 1 is a schematic block diagram showing the major the present invention.

Turning to FIG. 1., a block diagram is provided of the preferred embodiment of the present invention. A signal generator 12 produces a microwave signal that is directed by a waveguide 14 through a small horn antenna in a direction normal to the exterior surface of the tire 20. The tire has a number of layers of rubber 21, 22, and 23 backed by conducting steel belts 24 within the tire casing. These layers of rubber 21, 22, and 23 may or may not be substantially different in compound. The purpose of the system is to measure the total thickness of the rubber layers 21, 22, and 23. Alternatively, this system can be adapted to other applications in which it is necessary to measure the thickness of a layer of dielectric material backed by a layer of conductive material.

As will be discussed below, the frequency of the microwave signal is one of the factors that can be selected to control the range of rubber layer thicknesses that can be measured without ambiguity. However, experimentation has shown that either the X-band (approximately 8–12 Gigahertz) or the C-band (approximately 4 GHz) can be employed for the range of rubber thicknesses commonly encountered in retreading most tires. In the preferred embodiment, the microwave signal generator 12 is a Gunn diode oscillator (e.g. for X-band applications) or a voltage controlled oscillator (e.g. for C-band applications). For operation in the X-band, a rectangular waveguide having cross-sectional dimensions of 2.26 cm by 1.03 cm and a length of approximately 6 inches has been found to operate satisfactorily in its dominant $TE_{10}$ mode.

The microwave signal propagates along the length of the waveguide 14 and is directed through a small horn antenna at the waveguide port toward the tire 20. The horn antenna is located a predetermined distance from the surface of the tire. Each of the layers of rubber 21, 22, and 23 acts as a lossy, dielectric material that transmits a portion of the microwave signal and reflects a portion of the signal back toward the waveguide 14. The cumulative effect of the rubber layers and steel belts is to produce an attenuated reflected signal which is shifted in phase from the incident signal. A portion of this reflected signal is picked up by the horn antenna and back propagates along the length of the waveguide 14. Interference between the transmitted signal and the reflected signal results in a standing wave pattern within the waveguide 14. Since both the transmitted and reflected signals have the same frequency, the standing wave will have recurring minimums at each half wavelength (i.e. the spacing between adjacent minimums will be $\lambda/2$). However, the locations of these minimums along the length of the waveguide will shift as a function of the phase difference between the transmitted and reflected signals.

In the preferred embodiment, four coaxial probes 16 at predetermined positions along the length of the waveguide 14 permit four crystal detectors 18 to measure the amplitude of the standing wave voltage inside the waveguide 14. The crystal detectors 18 typically operate in their square law regions (i.e., output signal is proportional to the square of the standing wave voltage). Moreover, each of the detectors should be as close to identical in their characteristics as possible. The output signals from the crystal detectors 18 are amplified by an analog amplifier 32 and then digitized by an analog-to-digital convertor 34. The digitized signals can then be processed by a computer processor 36. The analog amplifier 32 and/or computer processor 36 can also be calibrated to compensate for any differences in the characteristics of the crystal detectors 18.

The computer processor 36 calculates the effective phase of the reflection coefficient by the voltages obtained from any three of the crystal detectors. The standing wave voltage at the location of the $n^{th}$ probe is:

$$V_n = V(1 + \rho e^{j(\theta - \Phi_n)}) \tag{1}$$

where V is the incident voltage, and $\Phi_n$ is the phase shift corresponding to the distance from the $n^{th}$ probe to the tire and back. $\rho$ and $\theta$ are amplitude and phase parameters respectively of the effective reflection coefficient of the tire. The phase $\theta$ of the reflection coefficient is the parameter to be determined by the computer processor 36.

$\Phi_n$ is calculated for each of the probes (n = 1, 2, and 3) on a one time basis as a function of the waveguide dimensions and the air gap between the waveguide port and the tire surface, as follows:

$$\Phi_n = \Phi_{guide} + \Phi_{air} = 4\pi \left( \frac{d_n}{\lambda_g} + \frac{d_{air}}{\lambda_{air}} \right) \tag{2}$$

where $d_n$ is the distance between the $n^{th}$ probe and the waveguide port; $\lambda_g$ is the guide wavelength; $d_{air}$ is the distance between the waveguide port and the tire (i.e. the air gap); and $\lambda_{air}$ is the wavelength in air (free space).

Next, equation (1) can be expanded to relate the output of any three of the probes:

$$|V_n| = |V| \sqrt{1 + \rho^2 + 2\rho \cos(\theta - \Phi_n)} \tag{3}$$

If the crystal detectors are operating in their square law regions, then their outputs will be proportional to $V_n^2$. To further simplify the analysis, define $S_n$ as Sin $\Phi_n$, and $C_n$ as Cos $\Phi_n$. Thus:

$$|V_n|^2 = C_n[2V^2\rho\cos\theta] + S_n[2V^2\rho\sin\theta] + [V^2(1+\rho^2)] \tag{4}$$

Calling the quantities inside the brackets A, B, and D respectively, and representing the left hand side as $P_n$ (power is proportional to the square of voltage), equation (4) simplifies to:

$$P_n = C_n A + S_n B + D \tag{5}$$

where:

$$A = 2V^2\rho\cos\theta \tag{6}$$

$$B = 2V^2\rho\sin\theta$$

$$D = V^2(1+\rho^2)$$

$$P_n = |V_n|^2$$

For the specific case of a three probe system (i.e. n = 1, 2, 3), this results in three simultaneous equations with three unknowns, namely A, B, and D:

$$D + C_1 A + S_1 B - P_1 = 0 \tag{7}$$

$$D + C_2 A + S_2 B - P_2 = 0$$

$$D + C_3 A + S_3 B - P_3 = 0$$

which can be solved as follows:

$$A = -\frac{P_1(S_3 - S_2) + P_2(S_1 - S_3) + P_3(S_2 - S_1)}{\sin(\Phi_3 - \Phi_2) + \sin(\Phi_1 - \Phi_3) + \sin(\Phi_2 - \Phi_1)} \tag{8}$$

$$B = \frac{P_1(C_3 - C_2) + P_2(C_1 - C_3) + P_3(C_2 - C_1)}{\sin(\Phi_3 - \Phi_2) + \sin(\Phi_1 - \Phi_3) + \sin(\Phi_2 - \Phi_1)}$$

$$D = \frac{P_1 \sin(\Phi_3 - \Phi_2) + P_2 \sin(\Phi_1 - \Phi_3) + P_3 \sin(\Phi_2 - \Phi_1)}{\sin(\Phi_3 - \Phi_2) + \sin(\Phi_1 - \Phi_3) + \sin(\Phi_2 - \Phi_1)}$$

It should be noted that the set of equations (7) must be independent. This means that the spacing between each of the probes should not be a multiple of $\lambda/2$.

Finally, from equations (6), the phase $\theta$ of the reflection coefficient can be determined as a function of A and B, as follows:

$$\theta = \arctan \frac{B}{A} \tag{9}$$

The remaining parameters of the standing wave can also be determined as functions of A, B, and D, if desired:

$$\rho = \frac{\sqrt{A^2 + B^2}}{2V^2}$$

$$V^2 = \frac{D + \sqrt{D^2 - A^2 - B^2}}{2}$$

The mathematics of this analysis is derived from the work done by R. Caldecott relating to measurment of reflection coefficients on electrical transmission lines. See, Caldecott, *The Generalized Multiprobe Reflectometer and Its Application to Automated Transmission Line Measurements* (IEEE Transactions on Antennas and Propagation, Vol AP-21, No. 4, July 1973).

Figure 2:
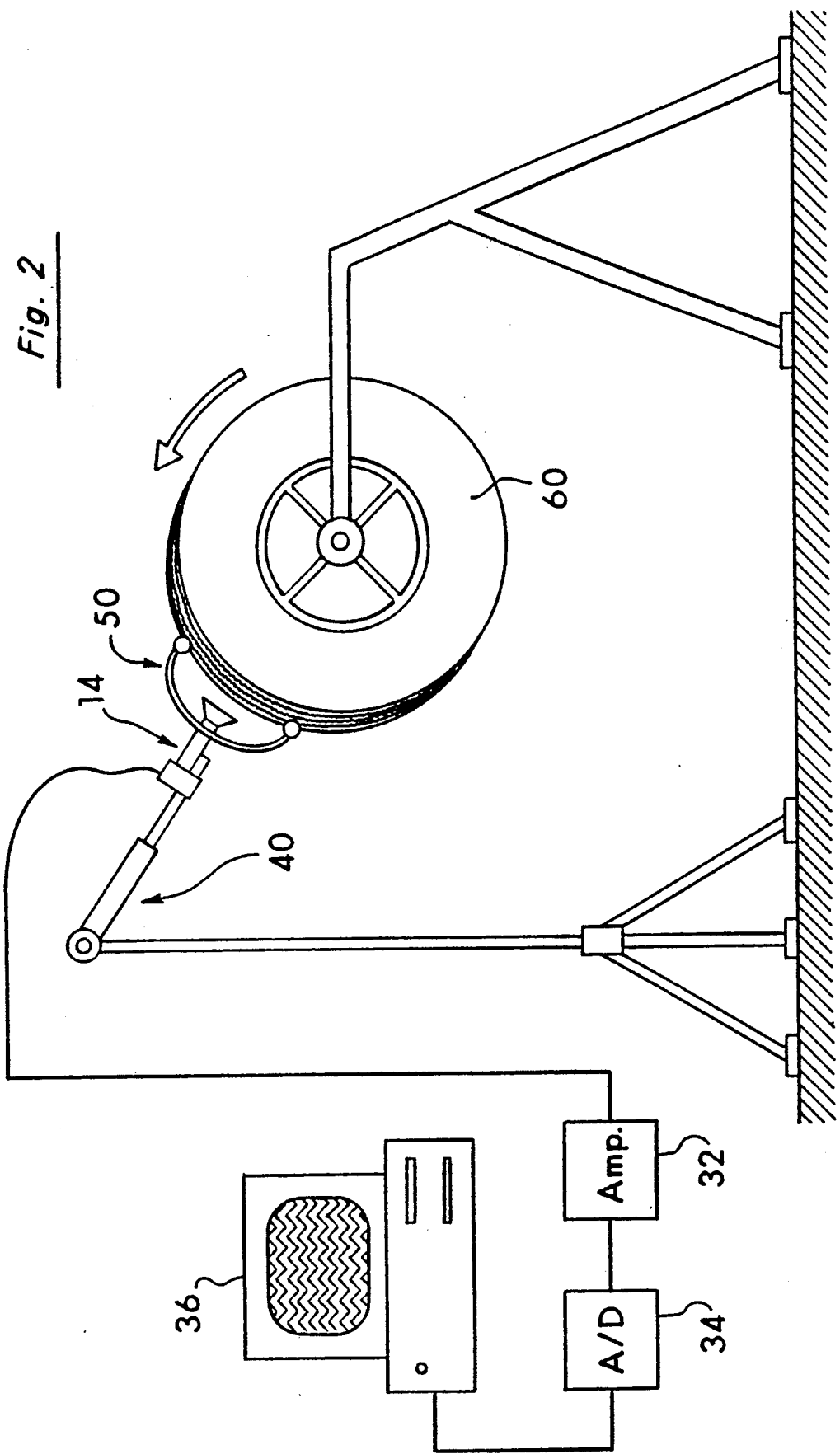
FIG. 2 is a simplified diagram showing the manner in which the present invention can be adapted to measure the of the layer of rubber on a rotating tire casing.

FIG. 2 shows a typical application of this sensor system to continually measure the thickness of the rubber layers on a rotating tire 60. Two spacing arms 50 cause the port of the waveguide 14 to ride at a substantially constant distance above the tire surface. The sensor assembly is mounted on and supported by a telescoping arm 40 which permits radial movement of the waveguide port in response to any variation in the tire radius. The arrangement shown in FIG. 2 can be used to provide continuous monitoring of the thickness of the rubber layers throughout the buffing process.

Figure 3:
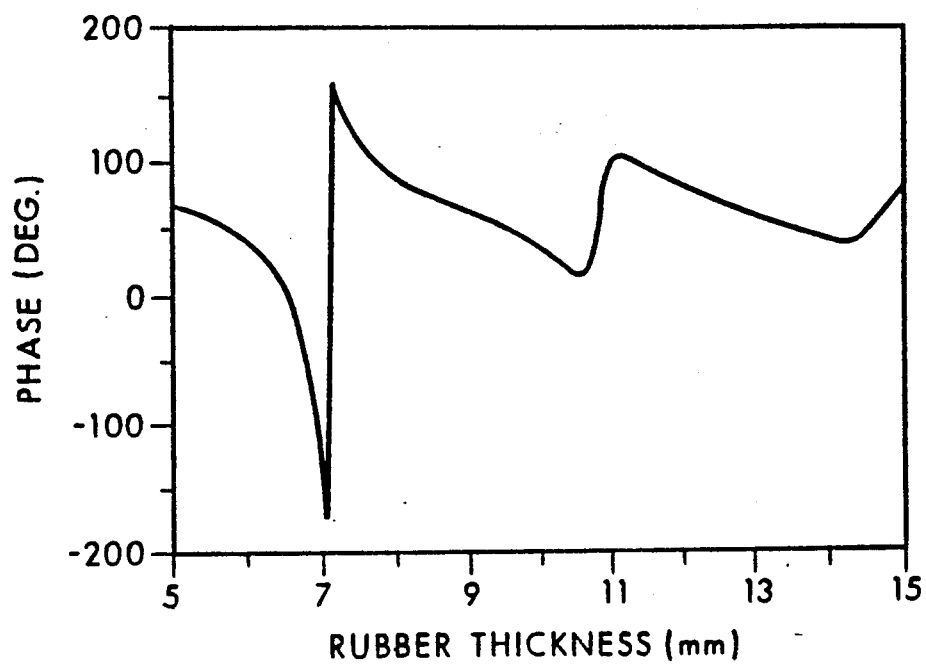
FIG. 3 is a graph showing the phase of the reflection coefficient as a function of the rubber thickness (and air gap) at 9.515 GHz (X-band) with an air gap of 0.5 and a rubber permittivity of 16.31−j2.3 on theoretical calculations.

FIG. 3 is a graph showing theoretical calculation of the phase $\theta$ of the reflection coefficient as a function of rubber thickness (plus the air gap) at 9.515 GHz (X-band) with an air gap of 0.5 cm and a rubber permittivity of $\epsilon_r= 16.31 - j2.33$. Experimental results have been shown to closely follow these theoretical calculations. FIG. 3 shows that as the rubber thickness decreases the phase $\theta$ remains positive until the rubber thickness reaches approximately 2.1 mm (5 mm air gap + 2.1 mm rubber thickness = 7.1 mm), at which point the phase undergoes an abrupt change into negative values. This corresponds to the point at which the arctangent function in equation (9) undergoes phase reversal from 180 degrees to $-180$ degrees. The other relative minima shown to the right in FIG. 3 correspond to other phase reversals in the arctangent function which occur at regular spacing intervals of $\lambda/2$. Moving to the right in FIG. 3, each subsequent relative minima is progressively less severe, and only the initial minima at 7.1 mm actually results in a negative phase. FIG. 3 suggests that this phase reversal can be used to stop the buffing process, particularly when this phase reversal is made to occur at a rubber thickness prescribed by the operator (i.e. 0.100 inches) by adjusting the air gap between the waveguide port and the tire surface.

Figure 4:
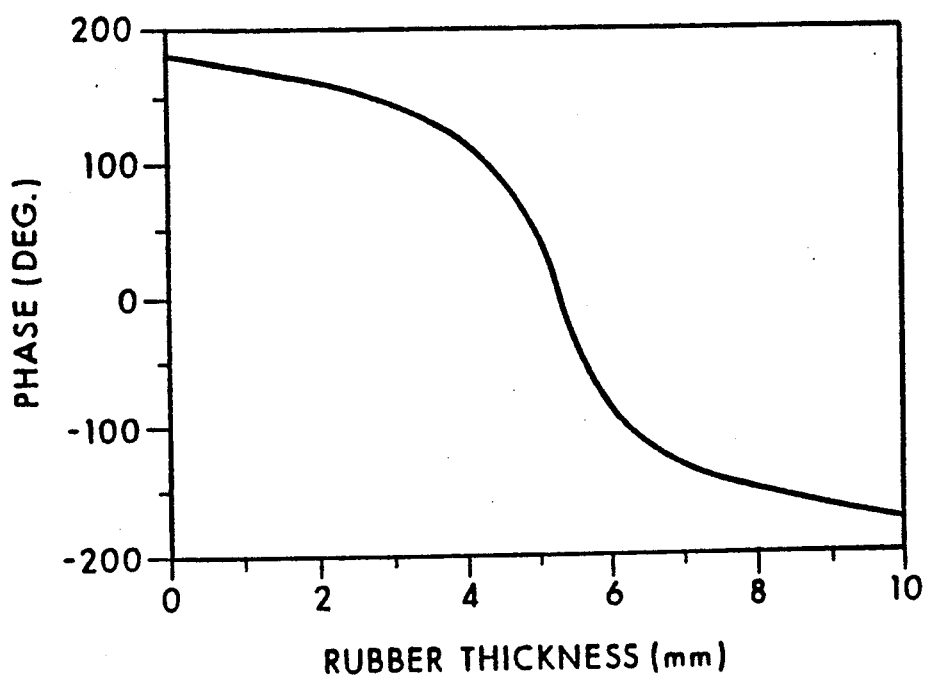
FIG. 4 is a graph showing the phase of the reflection coefficient as a function of rubber thickness at 4 GHz (C-band) with no air gap and a rubber of 12−j2.5, based on theoretical calculations.

An additional improvement can be attained by selecting the wavelength of the microwave signal such that only one phase reversal occurs throughout the range of rubber thicknesses to be measured. For example, FIG. 4 provides a graph based on theoretical calculations of the phase $\theta$ of the reflection coefficient as a function of the rubber thickness at 4 GHz (C-band) with no air gap and a rubber permittivity of $\epsilon = 12.5 - j2.5$. Again, these theoretical calculations have been closely confirmed by experimental results. The longer wavelength at 4 GHz permits unambiguous measurement of the rubber thickness at all times during the buffing process by effectively eliminating the recurring minima found in FIG. 4 for the relevant range of rubber thicknesses.

Figure 5:
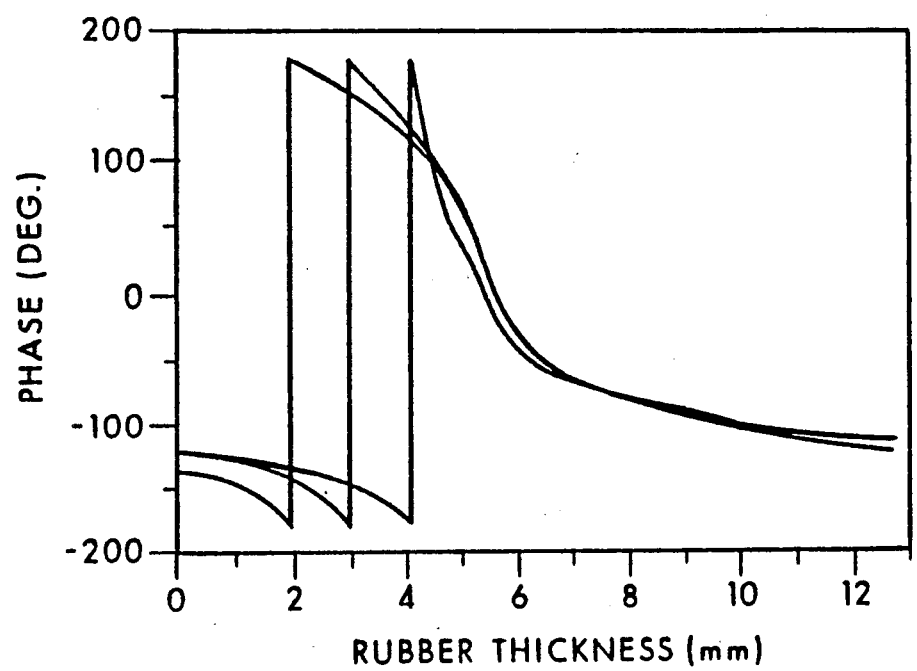
FIG. 5 is a graph showing the effect of variations in the air gap (19, 21, and 23 mm) on the phase of the reflection coefficient at 4 GHz (C-band), based on laboratory results.
Figure 6:
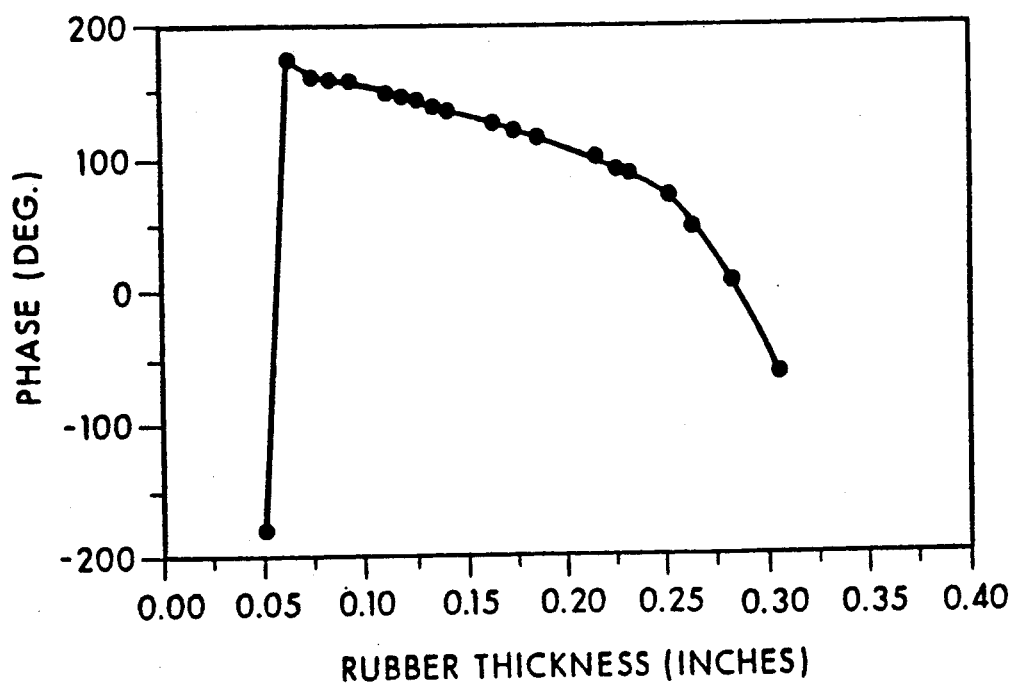
FIG. 6 is a graph showing the phase of the reflection coefficient as a function of rubber thickness at 4 GHz (C-band) with an air gap of 2.3 cm based on test results using a Michelin XZA-1 tire (DOT 347).
Figure 7:
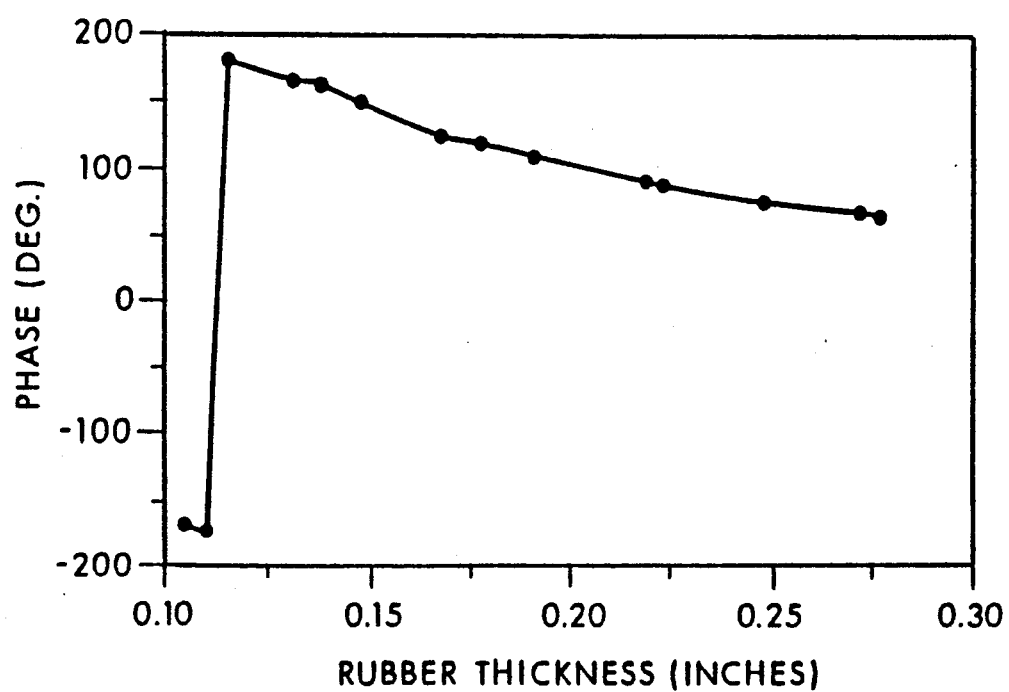
FIG. 7 is a graph showing the phase of the reflection coefficient as a function of rubber thickness at 4 GHz (C-band) with an air gap of 2.1 cm based on actual test results using a Michelin 11R22.5XZY tire (DOT 105).

FIGS. 5-7 demonstrate how these two features can be combined both to provide a means for unambiguous measurement of the rubber thickness during the buffing process, and to provide a rapid phase reversal at a predetermined rubber thickness to trigger a halt to the buffing process. FIG. 5 shows the effect of variations in the air gap (19, 21, and 23 mm) on the phase of the reflection coefficient at 4 GHz (C-band), based on laboratory results. FIG. 6 is a graph showing actual measurements of the phase of the reflection coefficient as a function of rubber thickness at 4 GHz (C-band) with an air gap of 2.3 cm using a Michelin XZA-1 tire (DOT 347). FIG. 7 is a graph showing the phase of the reflection coefficient as a function of rubber thickness at 4 GHz (C-band) with an air gap of 2.1 cm for a Michelin IIR22.5XZY tire (DOT 105). In each of these examples, the air gap between the waveguide port and the tire surface is adjusted to cause a sharp phase reversal to occur at a predetermined rubber thickness, as depicted at the left side of FIGS. 5-7. This air gap can either be determined by empirical testing or theoretical calculations using equations (8) and (7). To avoid the problems associated with recurring local minima as shown in FIG. 4, the wavelength should be long enough to have only one minima within the range of rubber thicknesses to be measured. As demonstrated in FIGS. 5-7, the C-band (approximately 4 GHz) has been found to be satisfactory for many types of tires. The buffing process typically begins toward the right side of the curve (see FIGS. 6-7) and progresses along the curve toward the left as the thickness of the rubber layer is reduced by buffing. The curve provides an unambiguous measurement of the rubber layer thickness at each point, thereby enabling the operator to judge how rapidly to proceed with the buffing operation. At the point where the phase shifts to negative values, the desired rubber thickness has been reached and the buffing process is terminated. This rapid phase reversal can be used to generate a signal for the operator or can be sensed by a control system to automatically end the buffing process.

The preceding discussion has assumed that the transmitting and receiving functions are combined in a single waveguide. This is the preferred embodiment of the present invention. However, it would be possible to implement the present invention with separate transmitter and receiver which determines the phase shift of the reflected signal with respect to the transmitted signal.

The above disclosure sets forth a number of embodiments of the present invention. Other arrangements or embodiments, not precisely set forth, could be practiced under the teachings of the present invention and as set forth in the following claims.

We claim:

1. A sensor for determining the thickness of the layer of rubber covering the steel belts within a tire, said sensor comprising:

means for generating a microwave signal;

waveguide means for transmitting said microwave signal toward the outer surface of said tire and receiving a portion of the microwave signal reflected from said tire to create a standing wave within said waveguide, said waveguide means having a port located at a predetermined distance adjacent to said tire;

detector means for measurement of said standing wave; and processing means for determining the phase shift of said reflected signal from data provided by said detector means, and for determining the thickness of said rubber layer as a predetermined function of said phase.

2. The sensor of claim 1 wherein said waveguide means comprises a substantially rectangular tube extending from said generator means to said port.

3. The sensor of claim 1 wherein said detector means comprises a plurality of crystal detectors extending along said waveguide means.

4. A sensor for determining the thickness of the layer of rubber covering the steel belts within a tire, said sensor comprising:

transmitter means for directing a microwave signal toward the outer surface of said tire, said transmitter means being located a predetermined distance from said tire surface;

means for measuring the phase difference between said transmitted signal and the microwave signal reflected by said tire, said phase measurement means being located a predetermined distance from said tire surface; and means for determining the thickness of said rubber layer as a predetermined function of said measured phase difference.

5. The sensor of claim 4 wherein said microwave signal has a frequency of approximately 8 to 12 Gigahertz.

6. The sensor of claim 5 wherein said microwave signal has a frequency of approximately 4 Gigahertz.

7. The sensor of claim 4 wherein said microwave frequency and the spacing between said tire surface and said phase measurement means is predetermined to cause a substantial change in said phase difference to occur at a predetermined thickness of said rubber layer.

8. The sensor of claim 1 wherein said microwave signal has a frequency of approximately 8 to 12 Gigahertz.

9. The sensor of claim 1 wherein said microwave signal has a frequency of approximately 4 Gigahertz.

10. The sensor of claim 1 wherein said microwave frequency and the spacing between said port means and said tire surface are predetermined to cause a substantial change in said phase of said reflected signal to occur at a predetermined rubber layer thickness.

11. A sensor for determining the thickness of the layer of rubber covering the steel belts within a tire, said sensor comprising:

a signal generator for generating a microwave signal;

a waveguide in the form of an elongated tube having a predetermined length extending from said signal generator to a port located at a predetermined distance adjacent to the outer surface of said tire, whereby the microwave signal transmitted by said signal generator and the microwave signal reflected from said tire combine within said waveguide to create a standing wave;

a plurality of crystal detectors at predetermined locations along the length of said waveguide, each crystal detector being adapted to generator an output signal indicative of the amplitude of said standing wave; and processing means for determining the phase shift of said reflected signal from said output signals provided by said crystal detectors, and for determining the thickness of said rubber layer as a predetermined function of said phase.

12. The sensor of claim 11 wherein said microwave signal has a frequency of approximately 8 to 12 Gigahertz.

13. The sensor of claim 11 wherein said microwave signal has a frequency of approximately 4 Gigahertz.

14. The sensor of claim 11 wherein the frequency of said microwave signal and the spacing between said port means and said tire surface are predetermined to cause a substantial change in said phase of said reflected signal to occur at a predetermined rubber layer thickness.

* * * * *